(12) United States Patent
Hess et al.

(10) Patent No.: US 6,228,226 B1
(45) Date of Patent: May 8, 2001

(54) PROCESS FOR WORKING UP CRUDE, LIQUID VINYL ACETATE

(75) Inventors: Stefan Hess, Gross-Berau; Michael Mark, Frankfurt, both of (DE); Melchior A. Meilchen, Houston, TX (US); Johann Stamm, Frankfurt (DE); Thomas Vernaleken, Weiterstadt (DE); Martin Wagner, Frankfurt (DE)

(73) Assignee: Celanese GmbH (DE)

( * ) Notice: Subject to any disclaimer, the term of this patent is extended or adjusted under 35 U.S.C. 154(b) by 0 days.

(21) Appl. No.: 09/316,320

(22) Filed: May 21, 1999

(30) Foreign Application Priority Data

Jun. 5, 1998 (DE) ................................ 198 25 254

(51) Int. Cl.⁷ .............................. B01D 3/34; C07C 67/54
(52) U.S. Cl. ................... 203/53; 203/61; 203/96; 203/99; 203/DIG. 21; 203/DIG. 19; 560/248
(58) Field of Search .............. 203/91–92, DIG. 19, 203/61, 53, 99, 96, DIG. 21; 560/248; 562/600

(56) References Cited

U.S. PATENT DOCUMENTS

| 3,905,875 | * | 9/1975 | Kronig et al. | 203/99 |
| 4,818,347 | * | 4/1989 | Roscher et al. | 203/DIG. 19 |
| 4,934,519 | * | 6/1990 | Wolf et al. | 703/96 |
| 5,066,365 | * | 11/1991 | Roscher et al. | 560/248 |

FOREIGN PATENT DOCUMENTS

| 2132299 | 5/1972 | (DE) . |
| 0072484 | 2/1983 | (EP) . |
| 0423658 | 4/1991 | (EP) . |

* cited by examiner

*Primary Examiner*—Virginia Manoharan
(74) *Attorney, Agent, or Firm*—Bierman, Muserlian and Lucas

(57) ABSTRACT

A process for working up crude, liquid vinyl acetate feed containing acetic acid, water and ethyl acetate and optionally smaller amounts of other impurities by distillation, wherein there is introduced into the distillation column, above the feed point of the crude, liquid vinyl acetate, 0.1 to 5% by weight of water, based on the crude, liquid vinyl acetate feed, and 0.1 to 60% by weight of acetic acid, based on the crude, liquid vinyl acetate feed.

16 Claims, 1 Drawing Sheet

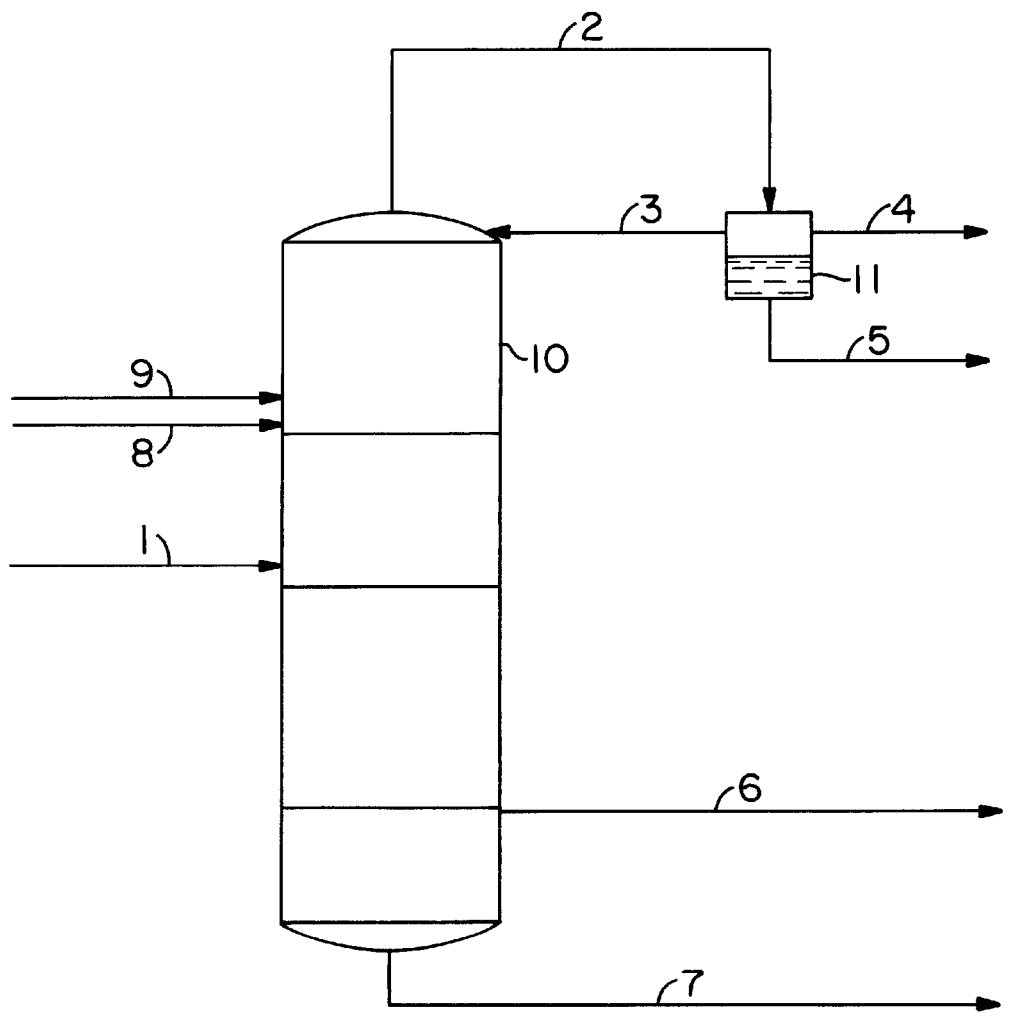

PROCESS FOR WORKING UP CRUDE, LIQUID VINYL ACETATE

A process for working up crude, liquid vinyl acetate containing acetic acid and water and also ethyl acetate and possible other impurities.

STATE OF THE ART

Processes for preparing vinyl acetate frequently produce a liquid, crude vinyl acetate which essentially consists of acetic acid and water and ethyl acetate and possibly other impurities. A product of this type can be obtained, for example, in the preparation of vinyl acetate by reacting ethylene and acetic acid and oxygen in the gas phase at elevated temperature and atmospheric or elevated pressure in the presence of a catalyst, cooling the gases leaving the reactor and/or scrubbing them with acetic acid. Such a preparation of vinyl acetate is generally carried out with excess acetic acid with the unreacted acetic acid being recirculated to the vinyl acetate preparation.

A workup of crude, liquid vinyl acetate which is accessible from such a preparation process and which still contains acetic acid and water and ethyl acetate and possibly other impurities is described in DE-B 1 768 412. In this process, the crude vinyl acetate is distilled azeotropically, recycling the vinyl acetate obtainable by condensation and phase separation of the overhead product withdrawing overhead the majority of the water together with vinyl acetate and recirculating enough vinyl acetate so that, as bottom product, an acetic acid is obtained which contains about 0.5 to 6% by weight of water. If appropriate, from this distillation, a liquid side stream can be taken off in which ethyl acetate is enriched. The vinyl acetate which is obtainable after condensation and phase separation of the gaseous overhead product contains about 100 to 500 ppm by weight of ethyl acetate.

A further known process for working up crude vinyl acetate is described in DE-C1 282 014 and DE-C1 668 063. In this case, in a first distillation column, the water, as an azeotropic mixture, and the by-product boiling lower than vinyl acetate are distilled overhead and the virtually water-free bottom product is distilled in a second distillation column, vinyl acetate being taken off at the top of the second distillation column, at least the majority of the by-product boiling above vinyl acetate being taken off from one or more enrichment zones between top and bottom and the acetic acid and, if appropriate, the remainder of the by-products, being taken off below the bottom enrichment zone or as bottom product. The vinyl acetate produced in the first column after condensation and phase separation is generally completely recirculated to the first column and vinyl acetate is only taken off from the top of the second column. According to the teaching of DE-C1 668 063, if the pressure in the first distillation column is increased from atmospheric pressure to 1 atm gauge, with about half the reflux rate, the same amount of water is discharged at the top of the second column. No information is given on the water content of the gaseous overhead product of the first column and the ethyl acetate content in the vinyl acetate taken off is about 1000 ppm.

DE-A 2 943 985 describes a process for separating off water from mixtures with vinyl acetate and acetic acid, in which a condensate obtained by cooling the gas mixture exiting from the reaction zone and containing the majority of the acetic acid, the vinyl acetate and the water and which contains a solution obtained by adsorption with acetic acid, which solution contains the non-condensed residual vinyl acetate and water, are applied to various plates in a distillation column. The overhead product can then contain approximately 3 to 5% by weight of water. Whether crude vinyl acetate containing ethyl acetate can be worked up in such a manner and what contents of ethyl acetate are then present in the vinyl acetate taken off is not disclosed in this DE-A.

Finally, DE-B 1 618 240 describes separating off ethyl acetate from vinyl acetate, in which separating an extractive distillation with water as entrainer is carried out. At a weight ratio of water to organic crude charge consisting of 99.8% by weight of vinyl acetate and 0.2% by weight of ethyl acetate, of 0.19:1 and at a reflux ratio of approximately 3:1, an overhead stream of purified vinyl acetate which contains less than 500 ppm by weight of ethyl acetate, based on vinyl acetate, is taken off. However, in this process, the vinyl acetate feed contains no significant quantities of water and/or acetic acid.

Furthermore, U.S. Pat. No. 3,404,177 discloses a process for separating vinyl acetate, water, acetic acid and, if appropriate, acetaldehyde, from gaseous reaction mixtures. Such reaction mixtures also contain ethylene, oxygen and $CO_2$. Ethyl acetate and its removal are not disclosed in this publication. Effects accompanied by water feed or azeotrope formation likewise not.

Finally, EP-B-0 072 484 discloses a process for working up by distillation crude, liquid vinyl acetate containing acetic acid and water and also ethyl acetate and possibly small amounts of impurities, an essentially vinyl-acetate- and water-containing mixture being obtained as overhead product, and essentially acetic acid being obtained as bottom product, and a side stream being taken off in which ethyl acetate is enriched, with the overhead product being condensed and, after phase separation, some of the vinyl acetate phase being recirculated as reflux to the distillation, which comprises introducing 0.1 to 5% by weight of water, based on the crude, liquid vinyl acetate feed, into the distillation above the feed point of the crude, liquid vinyl acetate. This known process leads to a sufficient dewatering in the distillation and to a reduction of the ethyl acetate content in the vinyl acetate obtained as overhead product.

DE-A-2 132 299 discloses that liquid vinyl-acetate- and ethyl-acetate-containing mixtures can be subjected to an extractive distillation using acetic acid as entrainer. The disclosed process leads to a reduction in the ethyl acetate content in the vinyl acetate taken off at the column top to approximately 200 ppm by weight. According to the teaching of DE-A-2 132 299, however, 60 g of acetic acid must be fed per 100 g of crude, liquid vinyl acetate used.

OBJECTS OF THE INVENTION

It is an object of the invention to provide an improved process for the purification of crude, liquid vinyl acetate containing acetic acid, water and ethyl acetate.

This and other objects and advantages of the invention will become obvious from the following detailed description.

THE INVENTION

The novel process of the invention for purifying crude, liquid vinyl acetate feed containing acetic acid, water and ethyl acetate and optionally small amounts of other impurities comprises distilling said crude vinyl acetate to remove vinyl acetate and water as overhead product and acetic acid as bottom product while recovering a side stream of enriched ethyl acetate, condensing the overhead product, effecting phase separation and recirculating some of the vinyl acetate as reflux in the distillation column, the improvement comprising introducing into the distillation column above the feed point of the crude, liquid vinyl acetate feed 0.1 to 5% by weight of water and 0.1 to 60% by weight of acetic acid, both based on the crude, liquid vinyl acetate feed.

Surprisingly, it has been found that the ethyl acetate content in the gases leaving the distillation at the top decreases and may be increased in the side stream leaving the distillation and the vinyl acetate discharge via this side stream is decreased if 0.1 to 5% by weight of water, based on the crude, liquid vinyl acetate feed, and 0.1 to 60% by weight of acetic acid, based on the crude, liquid vinyl acetate feed, are introduced into the distillation column above the feed point of the crude, liquid vinyl acetate.

The present invention therefore relates to a process for working up crude, liquid vinyl acetate containing acetic acid and water and also ethyl acetate and possibly small amounts of other impurities by distillation, a mixture essentially consisting of vinyl acetate and water being obtained as overhead product and essentially acetic acid being obtained as bottom product and a side stream being taken off in which ethyl acetate is enriched, and the overhead product being condensed and, after phase separation, some of the vinyl acetate phase being recirculated as reflux to the distillation column, which comprises introducing 0.1 to 5% by weight of water, based on the crude, liquid vinyl acetate feed, and 0.1 to 60% by weight of acetic acid, based on the crude, liquid vinyl acetate feed, into the distillation column above the feed point of the crude, liquid vinyl acetate.

Suitable for use in the process of the invention is, for example, crude, liquid vinyl acetate containing about 12 to 30% by weight of vinyl acetate, about 3 to 10% by weight of water, about 0.01 to 0.2% by weight of ethyl acetate and acetic acid to make up 100% by weight. Further impurities, for example diacetate, polymers, acetaldehyde and/or methyl acetate can also be present in small amounts, for example each in amounts of below 0.5% by weight. Impurities of this type can be formed in the vinyl acetate preparation or can have already been introduced into the vinyl acetate preparation together with the feed products.

Crude, liquid vinyl acetate suitable for use in the process of the invention can be obtained in various ways. For example, ethylene, oxygen or oxygen-containing gases and acetic acid can be reacted in a known manner in the gas phase at elevated temperature and atmospheric or elevated pressure at catalysts comprising noble metals and/or their compounds and the gases coming from this reaction can be cooled and/or scrubbed, for example with acetic acid or acetic-acid-containing scrubbing liquids, and the crude, liquid vinyl acetate thus obtainable can be used in the process of the invention.

BRIEF DESCRIPTION OF THE DRAWING

FIG. 1 is a diagrammatic representation of the apparatus used for the process of the invention.

DESCRIPTION OF THE PREFERRED EMBODIMENT

FIG. 1 is a diagrammatic representation of the workup of crude, liquid vinyl acetate where the crude, liquid vinyl acetate (stream 1) is introduced into a distillation column 10. Suitable distillation columns are, for example, those which comprise 50 to 110, preferably 55 to 105, plates and are operated at atmospheric pressure or slightly elevated pressure, for example at 0.1 to 0.5 MPa absolute, but preferably at atmospheric pressure. The crude, liquid vinyl acetate can be fed, for example, at a point which is in the middle region of column 10, preferably between the middle and the lowest third of column 10. Column 10 is operated in such a manner that, as overhead product (stream 2), an essentially vinyl-acetate and water-containing gaseous mixture is obtained and, as bottom product (stream 7), essentially acetic acid is obtained. In addition, a side stream (stream 6) is taken off, in which side stream ethyl acetate is enriched. Preferably, column 10 is operated so that a water content of 0.5 to 6% by weight and a vinyl acetate content of 1 to 30 ppm by weight are established in the acetic acid taken off the bottom (stream 7) and the side stream taken off below the feed point of the feed mixture (stream 6) contains, for example, up to 15% by weight of ethyl acetate in addition to fluctuating amounts of vinyl acetate, acetic acid and water. This side stream 6 can be taken off in the liquid or gaseous state and preferably, it is taken off in liquid form. The overhead product (stream 2) is condensed and separated in a phase separator 11 into an upper, water-saturated vinyl-acetate phase and a vinyl-acetate-saturated lower water phase which is removed as stream 5.

A phase separator of the customary type, e.g. a decanter, can be used. After phase separation has been accomplished, some of the water-saturated vinyl acetate phase is recirculated to the distillation column 10 as reflux (stream 3). The amount of the recycled water-saturated vinyl acetate can be controlled in such a manner that the desired water content, for example in the range from 0.5 to 6% by weight, is established in the bottom of column 10. For this, generally, a reflux ratio (ratio of recirculated vinyl acetate to vinyl acetate taken off) in the range from 1:1 to 8:1 is advantageous. The uncirculated water-saturated vinyl acetate (stream 4) is separated off and can, if necessary, be further purified. The bottom product produced in the distillation (stream 7), which generally comprises more than 90% by weight of acetic acid, can be recirculated to the process for preparing vinyl acetate, if appropriate, after separating off impurities, e.g. polymers.

Above the feed point of the crude, liquid vinyl acetate feed, water is introduced (stream 8). The source from which the water is introduced via stream 8 is not critical. The added water can also contain up to 5% by weight of organic constituents, based on the total amount of stream 8. Organic constituents of this type are, for example, vinyl acetate or ethyl acetate. The amounts of water which are introduced in this manner are relatively small, generally 0.1 to 5% by weight, preferably 0.1 to 2% by weight, based on the crude, liquid vinyl acetate feed. The operating procedure described hitherto, including any further purification of the vinyl acetate which has been separated off and the acetic acid arising in the bottom product, is disclosed, for example, by DE-B 1 768 412 and EP-B-0-072 484.

The measure to be performed of the invention in the work-up of crude, liquid vinyl acetate feed is then introducing water (stream 8), above the feed point of the crude, liquid vinyl acetate feed, in an amount which is not greater than the amount which is necessary to achieve a maximum water content in the gases leaving the distillation column 10 at the top (stream 2), and introducing acetic acid (stream 9) above the feed point of the crude, liquid vinyl acetate feed in an amount which is not greater than the amount which is necessary to achieve a maximum acetic acid content in the gases (stream 2) leaving the distillation column 10 at the top.

The source from which acetic acid is introduced via stream 9 is not critical. The acetic acid content in stream 9 is generally more than 80% by weight, and preferably more than 90% by weight. Further constituents of stream 9 are water with or without small amounts of organic compounds, such as ethyl acetate.

Even small amounts of water, generally 0.1 to 5, and preferably 0.1 to 2, % by weight, based on crude, liquid vinyl acetate feed, and acetic acid, generally 0.1 to 60, preferably 0.1 to 30, and particularly preferably 0.1 to 10, % by weight, based on crude, liquid vinyl acetate feed, which are introduced in this manner, increase the water content in the gases (stream 2) leaving the distillation at the top and thus lead to a sufficient dewatering in the distillation and cause a reduction in the ethyl acetate content in the vinyl acetate removed from the top of the distillation column 10. This procedure also causes the vinyl acetate content in the side stream (stream 6) taken off below the feed point of the crude, liquid vinyl acetate feed to be decreased. As a result, more vinyl acetate is produced via the top of the distillation column 10. A further advantage of the process of the invention is that the ethyl acetate content in the side stream (stream 6) is increased and thus vinyl acetate is produced via the top of the column 10 at a higher purity.

The addition of water causes the water content in the gas (stream 2) leaving the distillation at the top to increase, which leads to a sufficient dewatering in the distillation. Water can be used in this manner up to an amount such that the water content of the gases (stream 2) leaving the distillation column 10 at the top is a maximum of 7.3% by weight. It is known that the vinyl acetate/water azeotrope can have a maximum water content of 7.3% by weight (see Advances in Chemistry, Series 116, Azeotropic Data III, American Chemistry Society, Washington D.C., 1973). However, this value can generally not quite be achieved when carrying out the process of the invention in practice. The maximum achievable water content when the process of the invention is carried out in practice in the gases (stream 2) leaving the distillation column 10 at the top are about 6.8% by weight. Preferably, just enough water is added in the manner of the invention so that the water content in stream 2 is 6.7 to 6.9% by weight.

Adding acetic acid causes the ethyl acetate to separate off from vinyl acetate and water. Although this is disclosed by the prior art (DE-A-2 132 299), 60 g of acetic acid must be fed per 100 g of crude, liquid vinyl acetate feed.

The amounts of water and acetic acid to be introduced in the invention are relatively small. They are generally 0.1 to 5% by weight of water, based on the crude, liquid vinyl acetate feed and generally 0.1 to 60% by weight of acetic acid, based on the crude, liquid vinyl acetate feed. Preferably, the amount of water is 0.1 to 2% by weight, based on the crude, liquid vinyl acetate feed and the amount of acetic acid is preferably 0.1 to 30% by weight, and particularly preferably 0.1 to 10% by weight, based on the crude, liquid vinyl acetate feed. The amounts of water and acetic acid which are necessary in a specific individual case to achieve the highest possible water content and simultaneously the lowest possible ethyl acetate content, in the gases (stream 2) leaving the distillation at the top and, simultaneously, to achieve the highest possible ethyl acetate content in the side stream (stream 6) leaving the distillation, can, if appropriate, be determined by simple experiments. These amounts are dependent, for example, on the amounts of water, acetic acid and vinyl acetate in the liquid, crude vinyl acetate feed.

The amounts of acetic acid and water to be added in the invention can be introduced into the distillation column 10 in liquid form or as vapor. Acetic acid and water are added above the feed point of the crude, liquid vinyl acetate feed. If acetic acid and water are introduced below the feed of the crude, liquid vinyl acetate feed or together with the feed, satisfactory dewatering in the distillation is not observed and satisfactory reduction of the ethyl acetate content in the vinyl acetate separated off from the distillation overhead product is not observed. Therefore, it is essential for the process of the invention to perform the introduction of acetic acid and water above the feed of the crude, liquid vinyl acetate feed, generally 2 to 50 plates, preferably 10 to 35 plates, above the feed point of the crude, liquid vinyl acetate feed.

Acetic acid and water can be introduced on the same plate but both substances can also be introduced on different plates. The feed points which are necessary for the small amounts of acetic acid and water above the feed point of the crude, liquid vinyl acetate feed in a specific individual case to achieve the highest possible water content and simultaneously the lowest possible ethyl acetate content in the gases (stream 2) leaving the distillation at the top and, at the same time, to achieve an ethyl acetate content as high as possible in the side stream (stream 6) leaving the distillation, can be determined, if appropriate, by simple experiments.

The operating procedure of the invention has the following advantages:

The separation between vinyl acetate and ethyl acetate is improved which means, with vinyl acetate reflux unchanged, a vinyl acetate (stream 4) separated off from the distillation overhead product can be obtained which contains up to 40% less ethyl acetate than hitherto. If the ethyl acetate content in the vinyl acetate separated from the distillation overhead product is to be of the same order as hitherto, the process of the invention permits the distillation to be carried out at lower vinyl acetate reflux and/or permits the use of a liquid, crude vinyl acetate feed having a higher ethyl acetate content and/or permits the use of a shorter distillation column.

The amount of vinyl acetate in the ethyl acetate side stream take off (stream 6) is reduced which means that up to 60% less vinyl acetate is discharged via the side stream take off with the same amount of ethyl acetate in this side stream take off. As a result, the loss of vinyl acetate is considerably reduced.

It is particularly advantageous that the improvements achievable by the invention are achieved without increasing the expenditure on the distillation, e.g. with respect to number of plates, reflux amounts and energy requirements. It is surprising that these two effects, namely decreasing the ethyl acetate content in the vinyl acetate (stream 4) produced from the distillation overhead product and decreasing the vinyl acetate content in the ethyl acetate (stream 6) discharged via the side stream take off can be achieved by a simple measure, namely the addition of water and acetic acid by the invention.

In the following examples, there are described several preferred embodiments to illustrate the invention. However, it is to be understood that the invention is not intended to be limited to the specific embodiments.

EXAMPLES

A diagrammatic description of the examples given below is to be found in Drawing 1.

Example 1

Comparative Example 62 metric tons of a feed mixture of the composition below (stream 1) were added per hour to the 48th plate above the column foot into the distillation column 10 having 98 plates:

| | |
|---|---|
| Vinyl acetate | 25.00% by weight |
| Ethyl acetate | 0.07% by weight |
| Water | 7.00% by weight |
| Acetic acid | 67.50% by weight |
| Remainder | 0.43% by weight |

The feed mixture contained, as remainder, methyl acetate, acetaldehyde and other impurities, e.g. diacetates or polymers, each in amounts of less than 1,000 ppm by weight. The overhead product (stream 2) was condensed, cooled to 26° C. and passed to a phase separator 11. Of the vinyl acetate phase, 33.5 metric tons per hour were pumped as reflux (stream 3) to the top of the distillation column, and the remainder was taken off (stream 4). The composition of the vinyl acetate separated off (stream 4) was as follows:

| | |
|---|---|
| Ethyl acetate | 270 ppm by weight |
| Water | 1.20% by weight |
| Vinyl acetate | making up to 100% by weight |

An aqueous phase (stream 8) was pumped at a rate of 0.7 metric tons per hour to the 69th plate above the column foot and the composition of the aqueous phase (stream 8) was as follows:

| | |
|---|---|
| Water | 98.0% by weight |
| Vinyl acetate | 2.0% by weight |

The amount of water (stream 5) taken off from the phase separator 11 was 2.2 metric tons per hour and the composition of this water phase was as follows:

| | |
|---|---|
| Water | 98.0% by weight |
| Vinyl acetate | 2.0% by weight |

From the 17th plate above the column foot of column 10, a liquid side stream (stream 6) was taken off at a rate of 3.6 metric tons per hour having the composition

| | |
|---|---|
| Vinyl acetate | 2.0% by weight |
| Ethyl acetate | 1.0% by weight |
| Water | 10.0% by weight |
| Acetic acid | 87.0% by weight |

A liquid stream which essentially consists of acetic acid (stream 9) was pumped to the 11th plate above the column foot at a rate of 3.5 metric tons per hour and the composition of this acetic acid stream was as follows:

| | |
|---|---|
| Water | 10.1% by weight |
| Acetic acid | 89.9% by weight |

Example 2

Invention

The distillation column 10 described in Example 1 was operated under the same conditions as in Example 1. In contrast to Example 1, in this example, the acetic acid stream (stream 9) was conducted to the 69th plate above the column foot at a rate of 3.5 metric tons per hour and the composition of the vinyl acetate (stream 4) separated off was as follows:

| | |
|---|---|
| Ethyl acetate | 200 ppm by weight |
| Water | 1.20% by weight |
| Vinyl acetate | making up to 100% by weight |

From the 17th plate above the column foot of column 10, a liquid side stream (stream 6) was taken off at a rate of 3.6 metric tons per hour having the composition

| | |
|---|---|
| Vinyl acetate | 1.00% by weight |
| Ethyl acetate | 1.00% by weight |
| Water | 10.00% by weight |
| Acetic acid | 88.00% by weight |

As can be seen from Example 2, the addition of water and acetic acid according to the invention leads to a reduction of the ethyl acetate content in the vinyl acetate (stream 4) produced from the distillation overhead product and to a reduction of the vinyl acetate content in the ethyl acetate discharged via the side take-off (stream 6).

Various modifications of the process of the invention may be made without departing from the spirit or scope thereof and it is to be understood that the invention is intended to be limited only as defined in the appended claims.

What we claim is:

1. A process for purifying crude, liquid vinyl acetate feed containing acetic acid, water and ethyl acetate and optionally amounts of other impurities from the vinyl acetate production comprising distilling said crude vinyl acetate to remove vinyl acetate and water as overhead product and acetic acid as bottom product while recovering a side stream of enriched ethyl acetate, condensing the overhead product, effecting phase separation and recirculating some of the vinyl acetate as reflux in the distillation column, the improvement consisting essentially of introducing into the distillation column above the feed point of the crude, liquid vinyl acetate feed 0.1 to 5% by weight of water and 0.1 to 60% by weight of acetic acid, both based on the crude, liquid vinyl acetate feed.

2. The process of claim 1 wherein crude, liquid vinyl acetate feed contains 12 to 30% by weight of vinyl acetate, 3 to 10% by weight of water, 0.01 to 0.2% by weight of ethyl acetate and acetic acid to make up 100% by weight.

3. The process of claim 1 wherein the crude, liquid vinyl acetate feed additionally contains diacetates, polymers, acetaldehyde and/or methyl acetate, each in amounts below 0.5% by weight.

4. The process of claim 1 wherein the water is introduced so that the water content in the gases leaving distillation column at the top is in the range from 6.7 to 7.3% by weight.

5. The process of claim 1 wherein water is introduced in liquid form.

6. The process of claim 1 wherein water is introduced in the form of steam.

7. The process of claim 1 wherein water is introduced 2 to 50 plates above the feed point of the crude, liquid vinyl acetate feed.

8. The process of claim 1 wherein water is introduced 10 to 35 plates above the feed point of the crude, liquid vinyl acetate feed.

9. The process of claim 1 wherein 0.1 to 30% by weight of acetic acid, based on the crude, liquid vinyl acetate used, is introduced into the distillation column above the feed point of the crude, liquid vinyl acetate feed.

10. The process of claim 1 wherein 0.1 to 10% by weight of acetic acid, based on the crude, liquid vinyl acetate feed is introduced into the distillation column above the feed point of the crude, liquid vinyl acetate feed.

11. The process of claim 1 wherein acetic acid is introduced in liquid form.

12. The process of claim 1 wherein acetic acid is introduced in the form of vapor.

13. The process of claim 1 wherein acetic acid is introduced 2 to 50 plates above the feed point of the crude, liquid vinyl acetate feed.

14. The process of claim 1 wherein acetic acid is introduced 10 to 35 plates above the feed point of the crude, liquid vinyl acetate feed.

15. The process of claim 1 wherein acetic acid and water are introduced on the same plate of the 2 to 50 plates above the feed point of the crude, liquid vinyl acetate feed.

16. The process of claim 1, wherein acetic acid and water are introduced on the same plate of the 10 to 35 plates above the feed point of the crude, liquid vinyl acetate feed.

* * * * *